United States Patent [19]

Orlowski et al.

[11] Patent Number: 4,490,115

[45] Date of Patent: Dec. 25, 1984

[54] DENTAL MATERIAL COMPRISING ADDUCTS OF 3-METHACROYL-2-HYDROXYPROPYL ESTERS WITH DIISOCYANATES

[75] Inventors: Jan A. Orlowski, Altadena; David V. Butler, West Covina; Patrick D. Kidd, San Dimas, all of Calif.

[73] Assignee: Scientific Pharmaceutical, Inc., Duarte, Calif.

[21] Appl. No.: 485,894

[22] Filed: Apr. 18, 1983

Related U.S. Application Data

[60] Division of Ser. No. 267,608, May 27, 1981, Pat. No. 4,400,159, which is a continuation-in-part of Ser. No. 162,482, Jun. 24, 1980.

[51] Int. Cl.$^3$ .............................................. A61K 6/08
[52] U.S. Cl. ...................... 433/199; 106/35; 260/998.11; 433/201; 433/202; 433/217; 433/228; 523/115; 523/116; 523/117
[58] Field of Search .................. 260/998.11; 523/115, 523/116, 117, 118; 433/199, 201, 202, 217, 226, 228; 106/35

[56] References Cited

U.S. PATENT DOCUMENTS

| | | | |
|---|---|---|---|
| 4,323,348 | 4/1982 | Schmitz-Josten | 433/228 |
| 4,347,174 | 8/1982 | Nagase et al. | 523/116 |
| 4,379,695 | 4/1983 | Orlowski et al. | 433/217 |
| 4,383,826 | 5/1983 | Butler et al. | 433/228 |
| 4,400,159 | 8/1983 | Orlowski et al. | 433/202 |
| 4,406,625 | 9/1983 | Orlowski et al. | 433/228 |
| 4,420,306 | 12/1983 | Orlowski et al. | 433/228 |

Primary Examiner—Lorenzo B. Hayes
Attorney, Agent, or Firm—Cushman, Darby & Cushman

[57] ABSTRACT

Dental materials containing dimethacrylates having the following chemical structures:

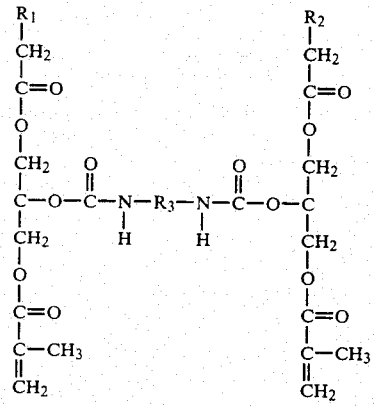

where $R_1$ and $R_2$ may be the same or different and are cyclohexyl or phenyl groups which may be substituted or unsubstituted; and $R_3$ is an aliphatic cycloaliphatic or aromatic group having 6 to 15 carbon atoms.

11 Claims, No Drawings

DENTAL MATERIAL COMPRISING ADDUCTS OF 3-METHACROYL-2-HYDROXYPROPYL ESTERS WITH DIISOCYANATES

CROSS REFERENCE TO OTHER CASES

This is a division of application Ser. No. 267,608, filed May 27, 1981, now U.S. Pat. No. 4,400,159 which is a CIP of Ser. No. 162,482, filed June 24, 1980.

BACKGROUND OF THE INVENTION

The present invention relates to a polymerizable compound, a polymer formed from this compound, a dental material containing this compound, a method for polymerizing this compound in situ on teeth, and a tooth comprising a polymer of this compound.

In recent years, the use of polymer-based dental materials became very prominent as they improved aesthetics and durability of restorations, faciliated application techniques and allowed great expansion of dental techniques in restorative, corrective and preventive applications. Especially important became filled restorative materials, cements, bonding agents, fissure sealers and orthodontic adhesives based on the polymerizable in situ aromatic and aliphatic methacrylates. The best properties in these materials have been obtained when the resin part of the composition is comprised of one or more of the following monomers:

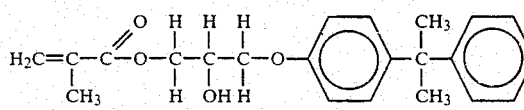

i.e., 2,2-bis[4'(3''-methacroyl-2''-hydroxypropoxy)-phenyl]propane (known in the industry as Bis-GMA), its adducts with various alkyl-isocyanates, such as adducts described in the Waller U.S. Pat. No. 3,629,187, the entire disclosure of which is hereby incorporated by reference and relied upon, and

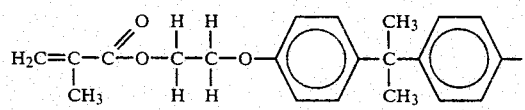

i.e., 2,2-bis[4'(2'''-methacroylethoxy)phenyl]propane (known in the industry as EBA).

These high molecular weight monomers are usually diluted with lower molecular weight polymethacrylates including dimethacrylates such as di-, tri- or tetraethylene glycol dimethacrylate, 1,6-hexanediol dimethacrylate, or trimethacrylates such as trimethylolpropane trimethacrylate. Other methacrylate monomers known to be used in certain restorative materials, cements, fissure sealers, bonding agents or orthodontic adhesives and claimed to improve mechanical, physical, clinical or aesthetic properties of materials are:

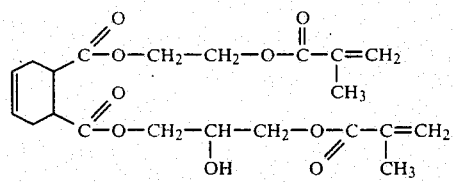

i.e., 2-methacroylethyl-3-methacroyl-2-hydroxypropyl tetrahydro (or hexahydro) phthalate and

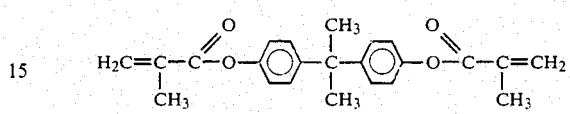

i.e., 2,2 bis-(4'-methacroylphenyl)propane (known in the industry as BADM).

In an attempt to improve methacrylate resin based dental materials, research efforts have been concentrated mainly on reducing their water sorption, as related to susceptibility to hydrolysis and staining, on minimizing their polymerization shrinkage and on improving their resistance to discoloration when exposed to sunlight.

These properties depend on the chemical structure of the monomer or monomers used in the formulation and their purity. In the formulations containing (besides the resin binder) a solid phase in the form of dispersed filler particles, the viscosity of the resin constitutes another important factor. The lower the viscosity of the alternative monomers that may be used in the formulation, other properties remaining similar or the same, the more filler may be incorporated in the formulation contributing to lower shrinkage, lower water sorption, better wear resistance and overall improved mechanical properties.

As it is recognized in the dental profession, the composite restoratives known up to now were unsuitable in most instances for use in posterior restorations, mainly because of their unsatisfactory wear resistance. This is especially true for Class II restorations as exposed the most to strong mastication forces. The typical properties of composite restoratives made according to presently known techniques are given below:

| | |
|---|---|
| Water Sorption as 37° C. | 0.7 mg/cm$^2$ |
| Compressive Strength | 30,000–40,000 psi |
| Diametral Tensile Strength | 3,480–4,600 psi* |
| Color Stability | Discoloration perceptible with difficulty |
| Hardness (Barcol) | 98 |
| Opacity/Translucency | 0.35–0.55* |

| -continued | |
|---|---|
| Filler/Resin ratio by Weight | 3.2:1 to 4.2:1 |

*Determined according to American Dental Associtaion Specification No. 27, JADA, Vol. 94, June, 1977.

In addition to the above-mentioned Waller U.S. Pat. No. 3,629,187, various polymeric dental materials have been described in the following U.S. Pat. Nos. 3,066,112 (Bowen); 3,179,623 (Bowen); 3,194,783 (Bowen); 3,194,784 (Bowen); 3,539,533 (Lee II et al.); 3,541,068 (Taylor); 3,597,389 (Taylor); 3,721,644 (Stoffey et al.); 3,730,947 (Stoffey et al.); 3,751,399 (Lee, Jr. et al.); 3,766,132 (Lee, Jr. et al.); 3,774,305 (Stoffey et al.); 3,860,556 (Taylor); 3,862,920 (Foster, et al.); 3,926,906 (Lee, II et al.); 4,102,856 (Lee, Jr.); and 4,107,845 (Lee, Jr. et al.). Further information on polymer based dental materials is given on pages 501–508 and 515–517 of the *Kirk-Othmer Encyclopedia of Chemical Technology*, Third Edition, Volume 7 (1979). The entire disclosures of the patents and the Kirk-Othmer reference set forth in this paragraph are hereby incorporated by reference and relied upon.

An important improvement in clinical performance of polymer-based dental restoratives may be achieved and their scope of applications greatly expanded if their water sorption is lowered, mechanical strength and hardness improved and filler/resin ratio significantly raised. Accordingly, there is a need in the art to develop polymerizable compounds which tend to overcome the shortcomings of the prior art polymerizable compounds used in dental materials.

SUMMARY OF THE INVENTION

The present invention relates to a compound of the following formula:

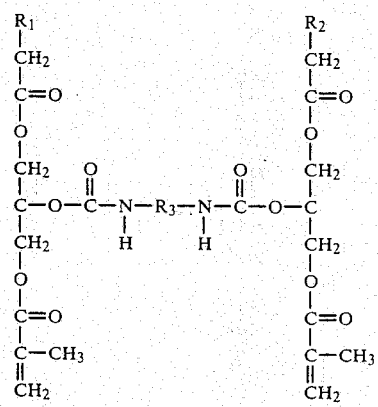

where $R_1$ and $R_2$ may be the same or different and are cyclohexyl or phenyl groups which may be substituted or unsubstituted; and $R_3$ is an aliphatic cycloaliphatic or aromatic group having 6 to 14 carbon atoms.

Other aspects of this invention relate to a polymer formed from this compound, a dental material (e.g., particularly a composite restorative material) containing this compound, a method for polymerizing this compound in situ on teeth and a tooth comprising a polymer of this compound.

DETAILED DESCRIPTION OF THE INVENTION

This invention relates to a dimethacrylate compound represented by the structure:

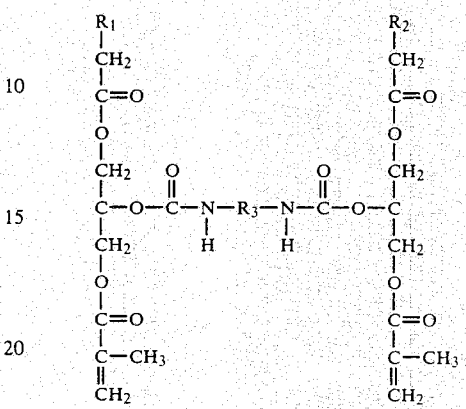

where $R_1$ and $R_2$ may be the same or different and are cyclohexyl or phenyl groups which may be substituted or unsubstituted; and $R_3$ is an aliphatic, cycloaliphatic or aromatic group having 6 to 14 carbon atoms.

Dimethacrylate compounds of this formula are referred to herein as compounds of the present invention. It will further be understood that structures given herein are intended to connote all possible stereoisomers and combinations thereof.

Although not intending to be strictly limited to any particular means for forming the compounds of the present invention, it is noted that these compounds may be described as adducts of 3-methacroyl-2-hydroxypropyl esters with diisocyanates. Thus, for example, an acetic acid derivative of the formula $R_4$—CH$_2$—COOH, where $R_4$ is $R_1$ or $R_2$, may be reacted with glycidyl methacrylate to form a hydroxy-containing ester intermediate of the formula:

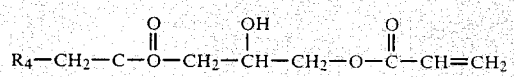

More particularly, the acetic acid derivative used to form this ester intermediate may be represented by the formula

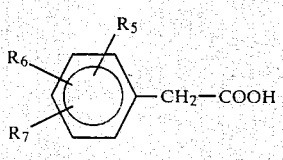

where

is a cyclohexyl or phenyl ring; and $R_5$, $R_6$ and $R_7$ may be the same or different and are preferably each hydrogen, but may also be alkyl or alkoxy groups having up to 12 carbon atoms. Such alkoxy groups may be represented by the formula —$OR_8$, where $R_8$ is an alkyl group as defined for $R_5$, $R_6$ and $R_7$, e.g., having up to 12 carbon atoms. Preferably, these $R_5$, $R_6$, $R_7$ and $R_8$ groups have up to 4 carbon atoms. Examples of $R_5$, $R_6$, $R_7$ and $R_8$ include methyl, ethyl, n-propyl, isopropyl, n-butyl, isobutyl, tert. butyl, straight or branched chain pentyl, straight or branched chain hexyl, straight or branched chain heptyl, straight or branched chain octyl, straight or branched chain nonyl, straight or branched decyl, straight or branched chain undecyl and straight or branched chain dodecyl. The groups $R_5$, $R_6$ and $R_7$ may be substituted in any possible position on the cyclohexyl or phenyl ring.

One or more of the above-mentioned hydroxy-containing ester intermediates may then be reacted with one or more diisocyanates of the formula

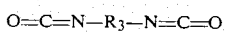

where $R_3$ is defined as above, to form compounds of the present invention. Examples of such diisocyanates include hexamethylene diisocyanate, octamethylene diisocyanate, decamethylene diisocyanate, undecamethylene diisocyanate, dodecamethylene diisocyanate, xylene-1,4-diisocyanate, xylene-1,3-diisocyanate, m-phenylene diisocyanate, p-phenylene diisocyanate, toluene-2,6-diisocyanate, mesitylene diisocyanate, durylene diisocyanate, benzidene diisocyanate, 1-methyl phenylene-2,4-diisocyanate, naphthylene-1,4-diisocyanate, naphthylene-1,5-diisocyanate, 3,3'-dimethyl-4,4'-diisocyanato diphenyl methane, 4,4'-diphenyl propane diisocyanate, dianisidine diisocyanate, cyclohexamethylene-1,4-diisocyanate, cyclohexamethylene-1,3-diisocyanate and 4,4'-diisocyanato dicyclohexyl methane. Preferred diisocyanates include hexamethylene diisocyanate and 4,4'-diisocyanato dicyclohexyl methane.

As mentioned previously an hydroxy-containing ester intermediate may be formed by reacting one or more compounds of the formula $R_4$—$CH_2$—$COOH$ with glycidyl methacrylate. This reaction may take place in the presence of a suitable electron donating catalyst such as triphenylphosphine and a polymerization inhibitor such as butylated hydroxytoluene (BHT). After removing excess glycidyl methacrylate from this reaction mixture, one or more diisocyanates may be added thereto to form one or more compounds of the present invention. Accordingly, compounds of the present invention may comprise various single compounds or mixtures of compounds. Preferred compounds of the present invention include adducts of phenylacetic acid/glycidyl methacrylate intermediates with 4,4'-diisocyanato dicyclohexyl methane or hexamethylene diisocyanate.

The dimethacrylates of the present invention may be combined with other polymerizable unsaturated materials, such as acrylic or methacrylic monomers or prepolymers, and polymerized. Thus, the dimethacrylates of the present invention may be polymerized to form either homopolymers or copolymers, e.g., containing at least 10% by weight of these dimethacrylate moieties. Preferably, copolymers of the dimethacrylates of the present invention may contain at least 40% by weight of these dimethacrylate moieties. As used herein, the term "moiety" shall connote an entire repeating polymeric unit and not some lesser fragment thereof.

Polymers of the dimethacrylates of the present invention are characterized in that they may have a high degree of crosslinking. Accordingly, these dimethacrylates may be added to mono-functional acrylic and methacrylic monomers and polymerized to form crosslinked polymers. Examples of these acrylic and methacrylic compounds include acrylic and methacrylic acid and esters thereof with alcohols containing, e.g., 1 to 4 carbon atoms. Examples of such acrylic and methacrylic esters include methylmethacrylate, ethylmethacrylate, butylmethacrylate, methylacrylate, ethylacrylate and butylacrylate.

Copolymers having an even higher degree of crosslinking may be produced by copolymerizing the dimethacrylates of the present invention with other polyfunctional acrylic ester or methacrylic ester monomers, i.e., monomers containing two or more acrylic or methacrylic functionalities. One class of these polyfunctional monomers includes monomers which are used as diluents in dental materials. Such polyfunctional acrylic ester or methacrylic ester monomers include alkylene glycol diacrylates, alkylene glycol dimethacrylates, polyalkylene glycol diacrylates, polyalkylene glycol dimethacrylates, alkanetriol triacrylates and alkanetriol trimethacrylates, e.g., containing from 8 to 18 carbon atoms. Examples of such monomers include ethylene glycol dimethacrylate, di-, tri- or tetraethylene glycol dimethacrylate, 1,6-hexanediol dimethacrylate, the dimethacrylate formed by the reaction of methacrylic acid with butanediol, trimethylolpropane trimethacrylate and the acrylic esters corresponding to these methacrylates, e.g. ethylene glycol diacrylate. As far as polyfunctional acrylates and methacrylates are concerned, these monomers are characterized by relatively low molecular weight (e.g., 339 or less) and low viscosity. The above-mentioned polyglycol dimethacrylates are further characterized by low surface tension.

Another class of polyfunctional acrylates and methacrylates includes the relatively high molecular weight (e.g., 364 or more) acrylic or methacrylic monomers used in dental compositions. Such polyfunctional compounds include, especially, dimethacrylates such as 2,2-bis[4'(3"-methacroyl-2"-hydroxypropoxy)phenyl]propane (i.e. Bis-GMA), 2,2-bis[4'(2"-methacroylethoxy)phenyl]propane (i.e., EBA), 2-methacroylethyl-3-methacroyl-2-hydroxypropyl tetrahydrophthalate, 2-methacroylethyl-3-methacroyl-2-hydroxypropyl hexahydrophthalate and 2,2-bis(4'-methacroylphenyl)propane (i.e. BADM). Further polyfunctional monomers containing up to four acrylic or methacrylic functionalities are described in the Stoffey et al. U.S. Pat. No. 3,721,644, the entire disclosure of which is hereby incorporated by reference and relied upon.

Accordingly, copolymers may be formed from polymerizable materials comprising at least one dimethacrylate of the present invention and, e.g., at least 10% by weight of one or more of the copolymerizable materials described herein.

Polymerization of the dimethacrylates of the present invention may be initiated by known means for initiating the polymerization of dimethacrylates such as heat, chemical means or electromagnetic-irradiation. Thus, in order to induce curing of dimethacrylates, a free-radical catalyst may be incorporated therein. Organic peroxide initiators, such as methyl ethyl ketone peroxide, t-butyl peroctoate, iso-propyl percarbonate, cumene hydroperoxide, dicumyl peroxide, and especially benzoyl peroxide, are preferred.

The ability of the initiator to cure dimethacrylates may be enhanced through the use of activators or accelerators. Thus, a peroxide initiator can be activated with a tertiary aromatic amine such as N,N-dimethyl-p-toluidine or N,N-bis(2-hydroxyethyl)-p-toluidine.

The amount of free-radical catalyst may be selected according to the curing rate desired. For instance, if a relatively slow curing rate is desired, a minimum catalytically effective amount, such as 0.5% by weight based on the polymerizable components, may be selected. On the other hand, when faster rates of cure are desired, greater amounts of free-radical catalyst, such as 4.0% or more by weight based on the polymerizable components, may be selected. Accordingly, the amount of catalyst may range from about 0.5 to about 4.0% by weight based upon the weight of the polymerizable components.

As with the free-radical catalyst, the amount of the activator selected may vary, e.g., from about 0.5 to about 4.0% by weight of the polymerizable components, depending upon the desired curing rate.

Polymerization of the dimethacrylates of the present invention may also be initiated by ultraviolet or visible light using known light activated polymerization initiators such as benzoin, benzoin methyl ether, benzil and other commercially available photoinitiators. For example, one may select from about 1% to about 5% by weight based on the polymerizable components of a sensitizer capable of initiating polymerization when exposed to UV light between about 3550 A. to about 3720 A.

The various components of a material containing a dimethacrylate of the present invention may be combined in any suitable manner. However, since chemically initiated polymerization starts immediately upon admixture of all three of (1) a methacrylate, (2) an initiator and (3) an activator, it is necessary to separate at least one of these components from the others until immediately before polymerization of the methacrylate. This separation may be achieved through the use of a two-package product, wherein various components of a material containing a dimethacrylate of the present invention are separately contained until the time of polymerization.

Therefore, the components of such a composition may be separated by means of a two-package product into two parts, one part containing the polymerization initiator and the other part containing the polymerization accelerator.

It is helpful to package polymerizable methacrylates with inhibitors, such as butylated hydroxytoluene (BHT) or hydroquinone methyl ether. Thus, BHT may be included in an amount from about 0.1 to about 0.3% by weight based on the polymerizable components to increase the storage stability of these polymerizable components.

Ultraviolet stabilizers such as 2-hydroxy-4-methoxybenzophenone (Cyasorb UV-9, a tradename of American Cyanamide) may be included to enhance the stability of the polymerizable components as well as polymers resulting therefrom. For example, from about 0.4 to about 1.6% by weight of Cyasorb UV-9 based on the weight of the polymerizable components may be used for this purpose.

In addition to polymerizable unsaturated material, inorganic or polymeric fillers may also be added to the monomers of the present invention prior to polymerization of these monomers. Accordingly, the term "polymer" as used herein may connote a polymeric matrix material which binds together various fillers.

Up to about 6.5 parts or even up to 8.5 parts of filler material per part of polymerizable unsaturated material may be included. Particular inorganic filler materials include silica materials (e.g., powdered quartz, barium glasses, borosilicate glasses, $SiO_2$, fumed silica and lithium aluminum silicate) and alumina materials (e.g., $Al_2O_3$). These inorganic filler materials may be treated with coupling agents, such as [3-(methacroyl)propyl]-trimethoxysilane, in order to assure the proper incorporation of filler into the polymeric matrix of the cured product. Other materials such as pigments may also be included in polymerizable materials comprising the dimethacrylates of the present invention.

It is noted that by varying the nature and proportions of curable compositions comprising one or more dimethacrylates of the present invention, a variety of such curable compositions as well as a variety of cured compositions resulting therefrom may be obtained. For example, curable compositions containing a relatively large amount of fillers, and relatively small amounts of low viscosity acrylic or methacrylic diluents, as well as minimum amounts catalysts and activators, may have a thick, doughlike consistency and a slow curing rate permitting working of the composition by molding and shaping before setting occurs. On the other hand, compositions containing little or no filler and relatively large amounts of low viscosity diluents, catalysts and accelerators may be flowable and fast curing, permitting brush-on application where little or no molding or shaping is required.

Polymerizable materials containing dimethacrylates of the present invention may now be described by way of examples of various dental materials. In this regard, composite restorative materials are given particular emphasis.

COMPOSITE RESTORATIVE MATERIALS

Composite restorative material, as the name implies, is a composite material of a polymerizable material and a suitable filler. These materials are capable of curing in situ on teeth to restore a hardened surface thereto. These materials are generally applied as a filling material to prepared or drilled teeth. Accordingly, composite restorative materials should be of a thick, workable consistency suitable for application to a prepared tooth and capable of being shaped or molded thereon before setting occurs. Thus, composite restorative materials are relatively slow curing.

The thick consistency of composite restorative materials, as well as the desirable properties of the cured product formed from these materials, are largely a function of the relatively large amounts of filler materials employed therein. More particularly, composite restorative materials may contain glass or ceramic fillers in excess of the polymerizable material employed therein.

When the polymerizable material of the composite restorative contains one or more dimethacrylate monomers of the present invention, the weight ratio of filler to polymerizable material may range from about 1.5:1 to about 6.5:1 or even up to about 8.5:1 and, most especially, from about 4:1 to about 6:1. Suitable ceramic or glass fillers include silica materials, such as powdered quartz, barium glasses, borosilicate glasses, $SiO_2$ and lithium aluminum silicate, and alumina materials, such as $Al_2O_3$. Since composite restorative materials must be capable of conforming to the confined space of prepared tooth and hardening therein to achieve restorative properties, the particle size of these fillers must be sufficiently small. Generally, the particle sizes of these fillers may range from about 1 to about 150 microns, preferably from about 1 to about 40 microns. The average particle size of these fillers is preferably less than about 25 microns. Suitably, composite restorative materials may contain a mixture of two or more fillers, such as a mixture of a ceramic filler (e.g. powdered quartz) and glass filler (e.g., powdered glass).

According to techniques well known in the art, the fillers of composite restorative materials may be treated with one or more organosilane coupling agents. These coupling agents are also sometimes referred to as finishing or keying agents and include materials such as [3-(methacroyl)propyl]trimethoxysilane. A sufficient coupling amount of such coupling agent may be a small amount such as from about 0.5 to about 1.0 part of coupling agent per 100 parts of filler. Methods for treating fillers with coupling agents are described, for example, in U.S. Pat. No. 3,066,112 (Bowen), wherein an aqueous solution of tris(2-methoxyethoxy)vinyl silane is catalyzed with sodium hydroxide to give a pH of 9.3 to 9.8, and the filler is treated with this solution, for example, one-half percent of silane per weight of fused quartz. A slurry so formed is dried at about 125° C. and cooled. Another technique for treating filler with a coupling agent is described in the passage extending from column 3, line 40 to column 4, line 4 of U.S. Pat. No. 3,862,920 (Foster et al).

As indicated previously, the filler, rather than polymerizable material, constitutes a major portion of the composite restorative material. Perhaps for this reason the polymerizable material in composite restoratives is sometimes referred to as a "binder".

The polymerizable materials for forming a composite restorative material may contain at least two monomeric components, termed herein a first monomer and a second monomer. This first monomer is at least one dimethacrylate monomer according to the present invention, and the second monomer is at least one relatively low molecular weight diluent monomer which, among other purposes, serves to reduce the overall viscosity of the composite restorative materials.

The first monomer of the polymerizable material may be present in an amount of from about 20 to about 90% by weight, preferably from about 70 to about 80% by weight, of the polymerizable material. The second monomer may be present in an amount from about 10 to about 80%, preferably from about 20 to about 30% by weight, of the polymerizable material.

As a second monomer, an acrylic or methacrylic diluent, which is used for this purpose in dental materials, may be selected. More particularly, this diluent may be a di- or trimethacrylate having from 10 to 18 carbon atoms. Diluents falling within this class of compounds include relatively low molecular weight (e.g., 339 or less) alkylene glycol dimethacrylates, polyalkylene glycol dimethacrylates and alkanetriol trimethacrylates. Particular examples of such diluents include di-, tri- or tetraethylene glycol dimethacrylate, 1,6-hexanediol dimethacrylate, and trimethylolpropane trimethacrylate. Triethylene glycol dimethacrylate is a preferred diluent.

The polymerizable material of composite restoratives may also contain at least one third monomer. This third monomer may be a relatively high molecular weight (e.g., 364 or more) polyfunctional acrylic or methacrylic monomer used in dental compositions. Such polyfunctional compounds include dimethacrylates such as 2,2-bis[4'(3"-methacroyl-2"-hydroxypropoxy)-phenyl]propane (i.e. Bis-GMA), 2,2-bis[4'(2"-methacroylethoxy)phenyl]propane (i.e., EBA), 2-methacroylethyl-3-methoacroyl-2-hydroxypropyl tetrahydrophthalate, 2-methacroylethyl-3-methacroyl-2-hydroxypropyl hexahydrophthalate and 2,2-bis(4'-methacroylphenyl)propane (i.e. BADM).

Although the third monomer constitutes a different class of materials than the first monomer, the first monomer and third monomer serve similar functions. Therefore, the third monomer may be used as a replacement for a portion of the first monomer, provided that the polymerizable material contains at least 20% by weight of the first monomer. This third monomer may be used in quantities close to the quantities of first monomer. For example, the weight ratio of the first monomer to the third monomer may range from about 3:5 to about 5:3. Accordingly, when the first monomer is present in an amount ranging from about 30 to about 50% by weight of the polymerizable material, the third monomer may also be present in an amount ranging from about 30 to about 50% by weight of the polymerizable material. Preferably, however, the weight percent of the first monomer is greater or equal to the weight percent of the third monomer.

In describing various composite restorative compositions, mention has been made of various specific compounds, such as triethylene glycol trimethacrylate and Bis-GMA, which fall into classes of compounds referred to as a second monomer or third monomer. However, it will be understood that the polymerizable material of the composite restorative material may contain further compounds which may fall within these categories of second or third monomers and/or may even fall in some separate and distinct category. For example, the polymerizable material may contain a small amount of methacrylic acid. However, due to the objectionable odor and properties of methacrylic acid, this monomer should not be present in quantities in excess of about 2% by weight (e.g., between about 1 and 2% by weight of the polymerizable material).

Composite restorative compositions may be cured by any suitable means, a chemically initiated system being preferred. This initiating system involves the use of a catalyst and an accelerator. Peroxide catalysts such as benzoyl peroxide and tertiary amine accelerators such as N,N-bis(2-hydroxyethyl)-p-toluidine are preferred. The amounts of catalyst and accelerator may each be from about 0.5 to about 2.0% by weight of the polymerizable materials.

Desirably, initial curing of the composite restorative material should take place in about 1 to about 2 minutes upon admixture of the components thereof in order to permit adequate mixing and manipulation of these components outside the mouth prior to application to a prepared tooth. However, final curing is desirably delayed for 4 to 6 minutes from the initial contacting of restorative components in order to permit proper molding and shaping inside the mouth. It is noted that template structures are sometimes used in this molding process. Composite restorative materials having such curing characteristics may enable a dentist to perform a complete restoration of a prepared tooth within about ten minutes, including grinding and polishing the restorative material after final setting.

Composite restorative materials may be packaged in any suitable manner. Preferably, a two-package system is used wherein each package contains filler and polymerizable material in roughly equal amounts, one package containing the catalyst and the other package containing the accelerator. However, other systems are also possible. For example, according to another two-package system, one package may contain both filler and catalyst and the other package may contain polymerizable material and accelerator. Another system involves packaging together each of the components excluding the catalyst component. When this system is used, polymerization can be initiated by introducing catalyst dropwise from a stock solution thereof. Such a stock solution is described in the Taylor U.S. Pat. No. 3,541,068 (Note particularly column 6, lines 23-50).

Whatever packaging system is used, it is helpful to package polymerizable materials with one or more polymerization inhibitors such as BHT in order to enhance storage life. Also, shelf life of components containing accelerators may be improved by removing traces of peroxides from these components with a reducing agent.

Cured composite restoratives containing at least one monomer according to the present invention have desirable properties and may be capable of holding up under strong mastication forces. For instance, these materials may have a water sorption at 37° C. of less than 0.5 mg/cm$^2$ (preferably 0.44 mg/cm$^2$ or less), a compressive strength of 40,000 psi or more; a diametral tensile strength of greater than 5,000 psi (preferably 5,300 psi or more), a hardness (Barcol) of greater than 98 (preferably 100 or more), and a linear shrinkage of 0.4% or less.

While particular emphasis has been devoted herein to the use of the monomers of the present invention in composite restorative materials, it will be understood that these monomers may also be used in other dental materials. Examples of these other dental materials are given in the Waller U.S. Pat. No. 3,629,187 (Note particularly column 11, line 26 to column 15, line 36) and in the *Kirk-Othmer Encyclopedia of Chemical Technology*, Third Edition, Volume 7 (1979), pages 501-508 and 515-517. Waller characterizes these materials as, e.g., dental cements, dental cavity liners and dental lacquers. Kirk-Othmer characterizes these materials as, e.g., unfilled tooth-restorative resins, pit and fissure sealants and adhesives.

In addition to one or more monomers according to the present invention, dental materials may contain one or more of the copolymerizable materials described herein, provided that such copolymerizable material is acceptable for oral application associated with dental treatment. Particular examples of such copolymerizable material include those methacrylate monomers mentioned herein with respect to composite restorative materials. The fillers described herein with respect to composite restorative materials may also be used in certain other dental materials.

Certain dental materials may contain various amounts of filler, while other dental materials contain no filler at all. For instance, the dental cements described in the Waller U.S. Pat. No. 3,629,187 may contain little or no filler if a transparent cement is desired, but these cements may contain up to about a 1:1 ratio of filler to polymerizable material if a translucent cement is acceptable. It is noted that fillers used in dental cements generally have smaller particle sizes (e.g., an average particle size of 10 microns or less) with respect to fillers used in composite restorative materials.

Dental materials may be cured by a photoinitiation technique using known light polymerization initiators or by chemically initiated systems including those systems using sulfinic acid activators.

In addition to fillers and polymerizable material, dental materials may contain other substances. For instance, pigments may be included. Also, ultraviolet absorbers or stabilizers may be included to lessen discoloration of the cured material. Furthermore, fluorides, bacteriostatic agents and antibiotics may also be included.

Dental materials may be applied to teeth in a variety of manners depending upon the nature of the material and the desired use. For instance, thick, slow-curing materials, such as composite restoratives, may be molded and shaped in the mouth before final curing takes place. On the other hand, flowable, fast-curing materials, such as cavity liners may be simply brushed on the surface of the treated tooth.

Dental materials such as restoratives, sealers, bonding agents, cements and orthodontic adhesives containing in their resin part 20-90% of the dimethylacrylate of the present invention exhibit most desirable properties, especially in respect to color stability, low water sorption, high mechanical strength and low polymerization shrinkage.

The following examples describe certain embodiments of the invention. It is to be understood that these examples are given only to illustrate the nature of the invention and should not, in any way, be understood as limiting the scope of this invention, defined in the claims.

EXAMPLE 1

330 g of glycidyl methacrylate (2.33 mole) and 272 g of phenylacetic acid (2 mole) were reacted at 100°-110° C. in the presence of triphenylphosphine catalyst and BHT inhibitor for 16 hours. The excess of glycidyl methacrylate was then removed in a stream of dry air and the reaction mixture cooled to 45° C.

256 g (0.97 mole) of 4,4'-diisocyanato dicyclohexyl methane has been introduced over 6 minutes while maintaining the temperature at 45°-50° C. The reaction mixture was then left for 72 hours at room temperature. The reaction product constituted a yellow viscous liquid. It is referred to hereafter as PAMC.

EXAMPLE 2

To 371 g (1.33 mole) of an adduct of glycidyl methacrylate and phenylacetic acid was obtained as described in Example 1. 109 g (0.65 mole) of hexamethylene diisocyanate was introduced over a one-hour period while maintaining the reaction temperature at the level of 45°-55° C. The mix was then allowed to stand at room temperature for 72 hours. The reaction product had a refractive index $n_D^{25}$ 1.492 and constituted a light yellow medium viscosity liquid. It is referred to hereafter as PAHD.

EXAMPLE 3

A dental composite restorative for use as a filling material in anterior and posterior restorations has been formulated as follows:

| Part A (Parts by Weight) | | Part B (Parts by Weight) |
| --- | --- | --- |
| 70 | PAMC | 70.9 |
| 12 | Hexanediol dimethacrylate | 12 |
| 13 | Triethyleneglycol dimethacrylate | 13 |
| 0.9 | Cyasorb UV-9 | 0 |
| 0.1 | BHT | 0.1 |
| 4 | N,N—bis(2'hydroxyethyl-p-toluidine) | 0 |
| 0 | Benzoyl peroxide | 4 |
| 200 | Powdered quartz below 44 microns, treated with methacroylpropyl trihydroxysilane | 200 |
| 300 | 2:1 mixture of powdered barium and borosilicate glasses below 44 microns, treated with methacroylpropyl trihydroxysilane | 300 |

Parts A and B when mixed in equal amounts cured in 120 seconds. The resulting material had the following characteristics.

| | |
| --- | --- |
| Water Sorption at 37° C. | 0.44 mg/cm$^2$* |
| Diametral Tensile Strength | 5,300 psi* |
| Compressive Strength | 40,000 psi |
| Hardness (Barcol) | 100 |
| Color Stability | Change perceptible with difficulty* |
| Opacity/translucency factor ($^C$0.70) | 0.45* |
| Linear Shrinkage | 0.4% |

*Determined according to method described in American Dental Association Specification No. 27, JADA Vol. 94, June, 1977

EXAMPLE 4

A dental composite restorative for use as filling material in anterior and posterior restorations has been formulated as follows:

| Part A (Parts by Weight) | | Part B (Parts by Weight) |
| --- | --- | --- |
| 75 | PAHD | 75.5 |
| 20 | Triethyleneglycol dimethacrylate | 20.9 |
| 0.9 | Cyasorb UV-9 | 0 |
| 0.1 | BHT | 0.1 |
| 4 | N,N—bis(2-hydroxyethyl) toluidine | 0 |
| 0 | Benzoyl Peroxide | 3.5 |
| 560 | Powdered quartz below 44 microns treated with methacroylpropyl trihydroxysilane | 500 |

Parts A and B when mixed in equal amounts cured in 120 seconds.

The properties of the curing material were virtually identical to those described in Example 3.

While the use of the monomers of the present invention has been described primarily with respect to dental materials, particularly composite restorative materials, it is noted that these monomers may also be used in other materials such as bone cements and UV curable inks. Thus, while certain representative embodiments and details have been shown for the purpose of illustrating the invention, it will be apparent to those skilled in the art that various changes and modifications may be made therein without departing from the spirit or scope of the invention. It will be further understood that the invention may comprise, consist essentially of or consist of the steps or materials recited herein.

What is claimed is:

1. A dental material comprising polymerizable unsaturated material comprising at least about 10% by weight of, a dimethacrylate of the following chemical structure:

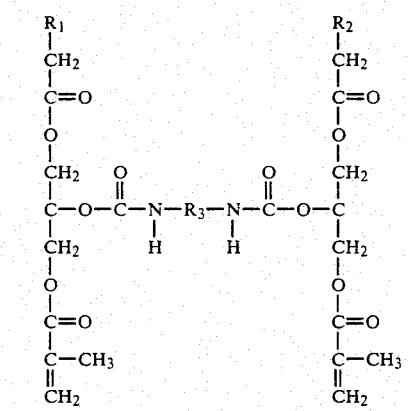

where $R_1$ and $R_2$ may be the same or different and are cyclohexyl or phenyl groups which may be substituted or unsaturated; and $R_3$ is an aliphatic, cycloaliphatic or aromatic group having 6 to 15 carbon atoms, the remainder of said polymerizable material being at least 10% by weight of at least one acrylic or a second and different methacrylic monomer acceptable for oral application associated with dental treatment.

2. A dental material according to claim 1, wherein said polymerizable unsaturated material comprises about 20 to about 90% by weight of said dimethacrylate and about 10 to about 80% by weight of at least one other polymethacrylate suitable for use in dental materials.

3. A dental material according to claim 2, wherein said other polymethacrylate is selected from the group consisting of diethylene glycol dimethacrylate, triethylene glycol dimethacrylate, tetraethylene glycol dimethacrylate, 1,6-hexanediol dimethacrylate, trimethylolpropane trimethacrylate, 2,2-bis[4'(3"-methacroyl-2"-hydroxypropoxy)phenyl]propane, 2,2-bis[4'(2"-methacroylethoxy)phenyl]propane, 2-methacroylethyl-3-methacroyl-2-hydroxypropyl tetrahydrophthalate, 2-methacroylethyl-3-methacroyl-2-hydroxypropyl hexahydrophthalate and 2,2 bis-(4'-methacroylphenyl)propane.

4. A dental material according to claim 1 comprising two parts capable of curing upon mixing of these parts, one of said parts comprising a peroxide-type polymerization initator and the other of said parts comprising a tertiary aromatic amine-type activator.

5. A dental material according to claim 1 comprising a light activated polymerization initiator capable of curing said dental material upon irradiation with ultraviolet or visible light.

6. A composite restorative material comprising glass or ceramic filler and polymerizable material,
said polymerizable material comprising at least one first monomer and at least one second monomer,
said first monomer being a dimethacrylate of the following structure:

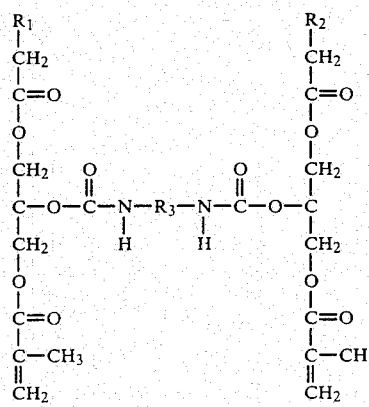

where $R_1$ and $R_2$ may be the same or different and are cyclohexyl or phenyl groups which may be substituted or unsubstituted; and $R_3$ is an aliphatic, cycloaliphatic or aromatic group having 6 to 15 carbon atoms, said second monomer being a diluent selected from the group consisting of di- and trimethacrylates having from 10 to 18 carbon atoms, said diluent further being selected from the group consisting of alkylene glycol dimethacrylates, polyalkylene glycol dimethacrylates and alkanetriol trimethacrylates, said at least one first monomer constituting at least 20% by weight of said polymerizable material, said at least second monomer constituting at least 10% by weight of said polymerizable material, and the weight ratio of said filler to said polymerizable material being from about 1.5:1 to about 8.5:1.

7. A composite restorative material according to claim 6, wherein said polymerizable material comprises from about 70% to about 80% by weight of said first monomer and about 20% to about 30% of said second monomer and the weight ratio of said filler to said polymerizable material is from about 4:1 to 6:1.

8. A composite restorative material according to claim 6, wherein both $R_1$ and $R_2$ of the dimethacrylate are unsubstituted phenyl and $R_3$ is hexamethylene or a dicyclohexyl methane group of the formula:

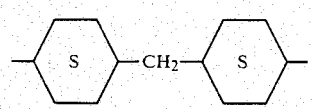

9. A composite restorative material according to claim 6 wherein the weight ration of said filler to said polymerizable material is from about 1.5:1 to about 6.5:1.

10. A composite restorative material according to claim 9 wherein said polymerizable material further comprises at least one third monomer selected from the group consisting of 2,2-bis[4'(3''-methacroyl-2''-hydroxypropoxy)phenyl]propane, 2,2-bis[4'(2''-methacroylethoxy)phenyl]propane, 2-methacroylethyl-3-methacroyl-2-hydroxypropyl tetrahydrophthalate, 2-methacroylethyl-3-methacroyl-2-hydroxypropyl hexahydrophthalate and 2,2-bis(4'-methacroylphenyl)propane, the weight ratio of said first monomer to said third monomer being from about 3:5 to 5:3.

11. A dental material according to claim 1 comprising a composite restorative material comprising glass or ceramic filler and polymerizable material, said polymerizable material comprising at least one first monomer and at least one second monomer, said first monomer being a dimethacrylate of the following structure:

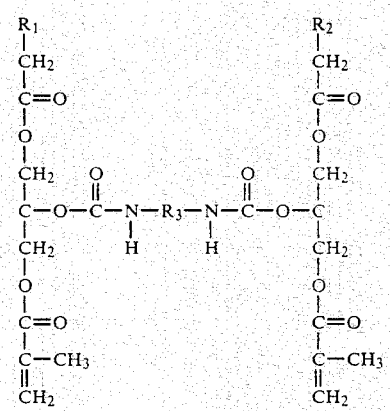

where $R_1$ and $R_2$ may be the same or different and are cyclohexyl or phenyl groups which may be substituted or unsubstituted; and $R_3$ is an aliphatic, cycloaliphatic or aromatic group having 6 to 16 carbon atoms, said second monomer being a diluent selected from the group consisting of di- and trimethacrylates having 10 to 18 carbon atoms, said diluent further being selected from the group consisting of alkylene glycol dimethacrylate, polyalkylene glycol dimethacrylates and alkanetriol trimethacrylates, said at least one first monomer constituting at least 20% by weight of said polymerizable material, said at least second monomer constituting at least 10% by weight of said polymerizable material, and the weight ratio of said filler to said polymerizable material being from about 1.5:1 to 8.5:1.

* * * * *